US009968443B2

(12) United States Patent
Bruchman et al.

(10) Patent No.: US 9,968,443 B2
(45) Date of Patent: *May 15, 2018

(54) VERTICAL COAPTATION ZONE IN A PLANAR PORTION OF PROSTHETIC HEART VALVE LEAFLET

(71) Applicant: W. L. Gore & Associates, Inc., Newark (DE)

(72) Inventors: William C. Bruchman, Camp Verde, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/869,524

(22) Filed: Apr. 24, 2013

(65) Prior Publication Data
US 2014/0172081 A1 Jun. 19, 2014

Related U.S. Application Data

(60) Provisional application No. 61/739,721, filed on Dec. 19, 2012.

(51) Int. Cl.
*A61F 2/24* (2006.01)

(52) U.S. Cl.
CPC .......... *A61F 2/2409* (2013.01); *A61F 2/2412* (2013.01); *A61F 2/2415* (2013.01); *A61F 2230/0023* (2013.01); *A61F 2230/0026* (2013.01); *A61F 2240/001* (2013.01)

(58) Field of Classification Search
USPC ....................... 623/2.12–2.18, 2.38
See application file for complete search history.

(56) References Cited

U.S. PATENT DOCUMENTS

| 3,953,566 | A |   | 4/1976 | Gore |
|---|---|---|---|---|
| 4,178,639 | A | * | 12/1979 | Bokros ............... A61F 2/2403 137/512.1 |
| 4,265,694 | A |   | 5/1981 | Boretos et al. |
| 5,628,791 | A |   | 5/1997 | Bokros et al. |
| 5,708,044 | A |   | 1/1998 | Branca |
| 6,174,331 | B1 |   | 1/2001 | Moe et al. |
| 6,283,994 | B1 |   | 9/2001 | Moe et al. |
| 6,283,995 | B1 |   | 9/2001 | Moe et al. |
| 6,287,334 | B1 |   | 9/2001 | Moll et al. |
| 6,328,763 | B1 |   | 12/2001 | Love et al. |
| 6,454,798 | B1 |   | 9/2002 | Moe |
| 6,482,228 | B1 | * | 11/2002 | Norred ..................... 623/2.17 |

(Continued)

FOREIGN PATENT DOCUMENTS

| CN | 102764169 | 11/2012 |
|---|---|---|
| FR | 2 591 100 | 6/1987 |

(Continued)

OTHER PUBLICATIONS

International Search Report for PCT/US2013/076688 dated Feb. 27, 2014, corresponding to U.S. Appl. No. 14/133,563, 5 pages.

(Continued)

*Primary Examiner* — Leslie Lopez

(57) ABSTRACT

Described embodiments are directed toward prosthetic valve leaflets of a particular shape that allows redundant coaptation height in the leaflets when a planar segment is present in each leaflet.

24 Claims, 10 Drawing Sheets

(56) References Cited

U.S. PATENT DOCUMENTS

| | | |
|---|---|---|
| 6,541,589 B1 | 4/2003 | Baillie |
| 6,562,069 B2 | 5/2003 | Cai et al. |
| 6,613,086 B1 | 9/2003 | Moe et al. |
| 6,666,885 B2 | 12/2003 | Moe |
| 6,916,338 B2 | 7/2005 | Speziali |
| 7,306,729 B2 | 12/2007 | Bacino et al. |
| 7,381,218 B2 | 6/2008 | Schreck |
| 7,462,675 B2 | 12/2008 | Chang et al. |
| 7,510,575 B2 | 3/2009 | Spenser et al. |
| 7,531,611 B2 | 5/2009 | Sabol et al. |
| 7,708,775 B2 | 5/2010 | Rowe et al. |
| 7,780,725 B2 | 8/2010 | Hauq et al. |
| 7,967,853 B2 | 6/2011 | Eidenschink et al. |
| 7,993,394 B2 | 8/2011 | Hariton et al. |
| 8,637,144 B2 | 1/2014 | Ford |
| 8,728,154 B2 | 5/2014 | Alkhatib |
| 8,870,948 B1 | 10/2014 | Erzberger et al. |
| 8,961,599 B2 | 2/2015 | Bruchman et al. |
| 9,101,469 B2 | 8/2015 | Bruchman et al. |
| 9,139,669 B2 | 9/2015 | Xu et al. |
| 9,144,492 B2 | 9/2015 | Bruchman et al. |
| 9,283,072 B2 | 3/2016 | Bruchman et al. |
| 9,398,952 B2 | 7/2016 | Bruchman et al. |
| 2002/0082687 A1 | 6/2002 | Moe |
| 2003/0114913 A1* | 6/2003 | Spenser ............... A61F 2/2412 623/1.11 |
| 2004/0024448 A1* | 2/2004 | Chang et al. ................. 623/1.42 |
| 2004/0039436 A1 | 2/2004 | Spenser et al. |
| 2004/0243222 A1 | 12/2004 | Osborne et al. |
| 2005/0027348 A1 | 2/2005 | Case et al. |
| 2005/0137682 A1 | 6/2005 | Justino |
| 2006/0122693 A1 | 6/2006 | Biadillah et al. |
| 2006/0290027 A1 | 12/2006 | O'Connor et al. |
| 2007/0010876 A1 | 1/2007 | Salahieh et al. |
| 2007/0021826 A1 | 1/2007 | Case et al. |
| 2007/0207186 A1* | 9/2007 | Scanlon et al. ............... 424/424 |
| 2008/0009940 A1 | 1/2008 | Cribier |
| 2008/0065198 A1 | 3/2008 | Quintessenza |
| 2008/0133004 A1 | 6/2008 | White |
| 2008/0195199 A1 | 8/2008 | Kheradvar |
| 2008/0220041 A1* | 9/2008 | Brito et al. .................... 424/423 |
| 2009/0240320 A1 | 9/2009 | Tuval et al. |
| 2010/0036021 A1 | 2/2010 | Lee et al. |
| 2010/0082094 A1 | 4/2010 | Quadri et al. |
| 2010/0137998 A1 | 6/2010 | Sobrino-Serrano et al. |
| 2010/0168839 A1 | 7/2010 | Braido et al. |
| 2010/0185274 A1 | 7/2010 | Moaddeb et al. |
| 2010/0191320 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2012/0101567 A1 | 4/2012 | Jansen |
| 2012/0101571 A1 | 4/2012 | Thambar et al. |
| 2012/0130471 A1 | 5/2012 | Shoemaker et al. |
| 2012/0185038 A1 | 7/2012 | Fish |
| 2012/0323315 A1 | 12/2012 | Bruchman et al. |
| 2014/0031924 A1 | 1/2014 | Bruchman et al. |
| 2014/0031927 A1 | 1/2014 | Bruchman et al. |
| 2014/0172078 A1 | 6/2014 | Bruchman et al. |
| 2014/0172083 A1 | 6/2014 | Bruchman et al. |
| 2014/0180400 A1 | 6/2014 | Bruchman et al. |
| 2014/0236289 A1 | 8/2014 | Alkhatib |
| 2014/0324164 A1 | 10/2014 | Gross et al. |
| 2015/0142100 A1 | 5/2015 | Morriss et al. |
| 2016/0157998 A1 | 6/2016 | Bruchman et al. |

FOREIGN PATENT DOCUMENTS

| | | |
|---|---|---|
| GB | 2312485 A | 10/1997 |
| WO | 00/62716 | 10/2000 |
| WO | 2008/097592 | 8/2008 |
| WO | WO2009029199 A1 | 3/2009 |
| WO | 2010057262 A8 | 5/2010 |
| WO | 2011109450 A2 | 9/2011 |
| WO | 2011109801 A2 | 9/2011 |
| WO | 2012040643 A2 | 3/2012 |
| WO | 2012/082952 | 6/2012 |
| WO | 2012/110767 | 8/2012 |
| WO | 2012/167131 | 12/2012 |
| WO | 2014/018432 | 1/2014 |

OTHER PUBLICATIONS

International Search Report for PCT/US2013/074962 dated Feb. 27, 2014, corresponding to U.S. Appl. No. 13/833,650, 4 pages.

International Search Report for PCT/US2013/068390 dated Apr. 29, 2014, corresponding to U.S. Appl. No. 13/835,988, 7 pages.

International Search Report for PCT/US2013/075275 dated Feb. 27, 2014, corresponding to U.S. Appl. No. 13/843,196, 5 pages.

International Search Report for PCT/US2013/068780 dated Feb. 27, 2014, corresponding to U.S. Appl. No. 13/869,878, 4 pages.

Clough, Norman E. Introducing a New Family of Gore™ ePTFE Fibers (2007).

International Search Report for PCT/US2013/076504 dated Apr. 28, 2014, corresponding to U.S. Appl. No. 14/133,491, 7 pages. (previously submitted on Aug. 7, 2014).

International Search Report for PCT/US2013/071632 dated Apr. 28, 2014, corresponding to U.S. Appl. No. 13/841,334, 6 pages. (previously submitted on Aug. 7, 2014).

International Search Report for PCT/US2013/075380 dated Mar. 6, 2014, corresponding to U.S. Appl. No. 13/869,524, 5 pages. (previously submitted on Aug. 7, 2014).

International Search Report for PCT/US2013/075380 dated Mar. 3, 2014, corresponding to U.S. Appl. No. 13/869,524, 5 pages. (previously submitted on Aug. 7, 2014).

International Search Report for PCT/US2013/046389 dated Jan. 21, 2014, corresponding to U.S. Appl. No. 13/797,633; 18 pages.

International Search Report for PCT/US2013/051431 dated Jan. 20, 2014, corresponding to U.S. Appl. No. 13/797,526; 6 pages.

\* cited by examiner

US 9,968,443 B2

VERTICAL COAPTATION ZONE IN A PLANAR PORTION OF PROSTHETIC HEART VALVE LEAFLET

CROSS-REFERENCE TO RELATED APPLICATIONS

This application claims priority to provisional application Ser. No. 61/739,721 filed Dec. 19, 2012, which is herein incorporated by reference in its entirety.

FIELD

The present disclosure relates generally to prosthetic valves and more specifically, to the geometry of flexible synthetic heart valve leaflets.

BACKGROUND

The durability of synthetic materials used for heart valve leaflets under the repetitive loads of the opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

The durability of the valve leaflets is also a function of the character of bending by the leaflet during the opening-closing cycle. Small radius bends, creases and intersecting creases, can produce high stress zones in the leaflet. These high stress zones can cause the formation of holes and tears under repetitive loading.

Prosthetic valves may be delivered using surgical or transcatheter techniques. A surgical valve is implanted into a patient using open-heart surgical techniques. The surgical valve is usually manufactured to have a fixed diameter as opposed to a transcatheter valve which is required to attain a range of diameters for access and delivery. The surgical valve is usually provided with a sewing cuff about a perimeter of the valve to allow for suturing to the native tissue orifice.

In addition to the valve durability issues discussed above, the transcatheter valve must also be able to withstand the handling and deployment stresses associated with being compressed and expanded A "preferred" shape of synthetic heart valve leaflets has been described many times, but each is different from the others. The various transient three dimensional shapes range from spherical or cylindrical to truncated conical intersections with spheres, and an "alpharabola". The shape most often described as "preferable" is modeled after the native human aortic valve. Though nature dictates the optimum shape for the native tissues to form a heart valve, we have discovered this is not true for synthetic materials.

SUMMARY

Described embodiments are directed to an apparatus, system, and methods for valve replacement, such as cardiac valve replacement. More specifically, described embodiments are directed toward flexible leaflet valve devices in which the leaflets have a planar central zone. The presence of the planar zone may be determined when the valve is not under pressure. The planar zone is present in the form of a truncated isosceles triangle or an isosceles trapezoid defining a truncated top. The width of the truncated top at the free edge of the leaflet is chosen so that, in the closed and fully pressurized condition, full coaptation of the leaflets is achieved.

A prosthetic valve is provided having a leaflet frame and a plurality of leaflets. The leaflets are coupled to the leaflet frame. Each leaflet includes a free edge and a base. Each leaflet has a planar zone in a central region, wherein the planar zone is substantially planar, wherein the planar zone defines a shape having an area. The area is larger nearer the base than the free edge. The planar zone extends to the free edge defining a truncated top having a top width as measured along the free edge greater than zero. Each leaflet has a coaptation zone defined by an area adjacent the free edge that is in contact with an adjacent leaflet when the leaflets are in a closed position. A coaptation height is defined as a length of the coaptation zone measured in an axial direction, wherein the coaptation height is greater than zero.

A method of forming a prosthetic heart valve, comprises: providing a leaflet frame having a generally tubular shape, the leaflet frame defining a plurality of leaflet windows wherein each of the leaflet windows includes two leaflet window sides, a leaflet window base, and a leaflet window top; providing a film; wrapping the film about the leaflet frame bringing more than one layer of the film into contact with additional layers of the film defining at least one leaflet extending from each of the leaflet windows; and bonding the layers of film to itself and to the leaflet frame, wherein each leaflet has substantially a shape of an isosceles trapezoid having two leaflet sides, a leaflet base and a free edge opposite the leaflet base, wherein the two leaflet sides diverge from the leaflet base, wherein the leaflet base is substantially flat, wherein the leaflet base is coupled to the window base and wherein each of the two leaflet sides are coupled to one of the two window sides providing a generally annular support structure, each leaflet having a planar zone in a central region, wherein the planar zone is substantially planar, wherein the planar zone defines a shape having an area, wherein the area is larger nearer the base than the free edge, wherein the planar zone extends to the free edge defining a truncated top having a top width as measured along the free edge greater than zero, each leaflet having a coaptation zone defined by an area adjacent the free edge that is in contact with an adjacent leaflet when the leaflets are in a closed position, defining a coaptation height as a length of the coaptation zone measured in an axial direction, wherein the coaptation height is greater than zero.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

DETAILED DESCRIPTION

Figure 1A:
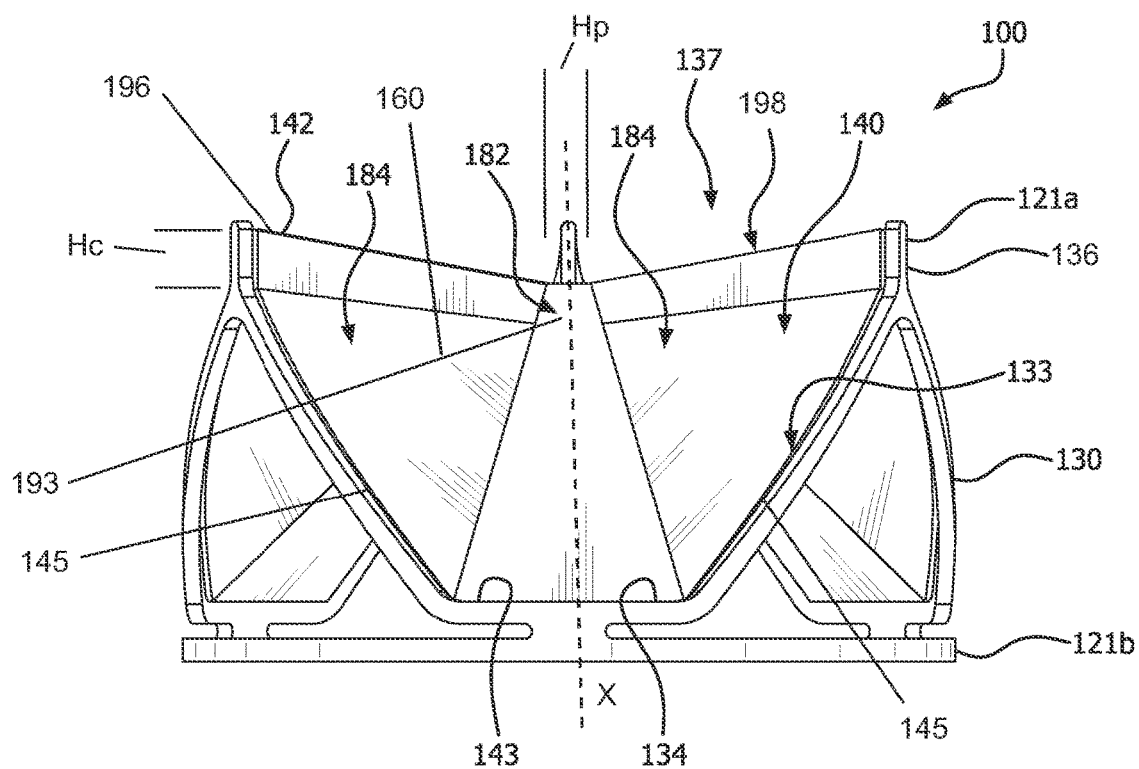
FIG. 1A is a side view of a prosthetic valve in accordance with an embodiment.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The term leaflet window is defined as that space that a frame defines from which a leaflet extends. The leaflet may extend from frame elements or adjacent to frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, couple, connect, attach, adhere, affix, or bond, whether directly or indirectly, and whether permanently or temporarily.

Embodiments herein include various apparatus, systems, and methods for a prosthetic valve suitable for surgical and transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

The embodiments presented herein are related to controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading.

The design specified in the current disclosure is intended to place the leaflets made from synthetic materials under a minimized stress condition as compared to those based on copies of the native valve. This is partially accomplished through reduced buckling in the leaflet material. It has been discovered that two features of leaflet shape are of particular importance in minimizing buckling and crease formation. They are of particular importance in thin, high-modulus leaflets, since the bending in these materials tends to be cellophane-like. If the leaflet bending is unrestricted, not only do creases form, but crease intersections lead to formation of large transient three dimensional structures that oppose bending and slow down the leaflet motion, both in opening and closing. In accordance to embodiments herein, features are provided in the valve leaflets that allows a redundant coaptation zone in the leaflets.

Valve

Figure 1B:
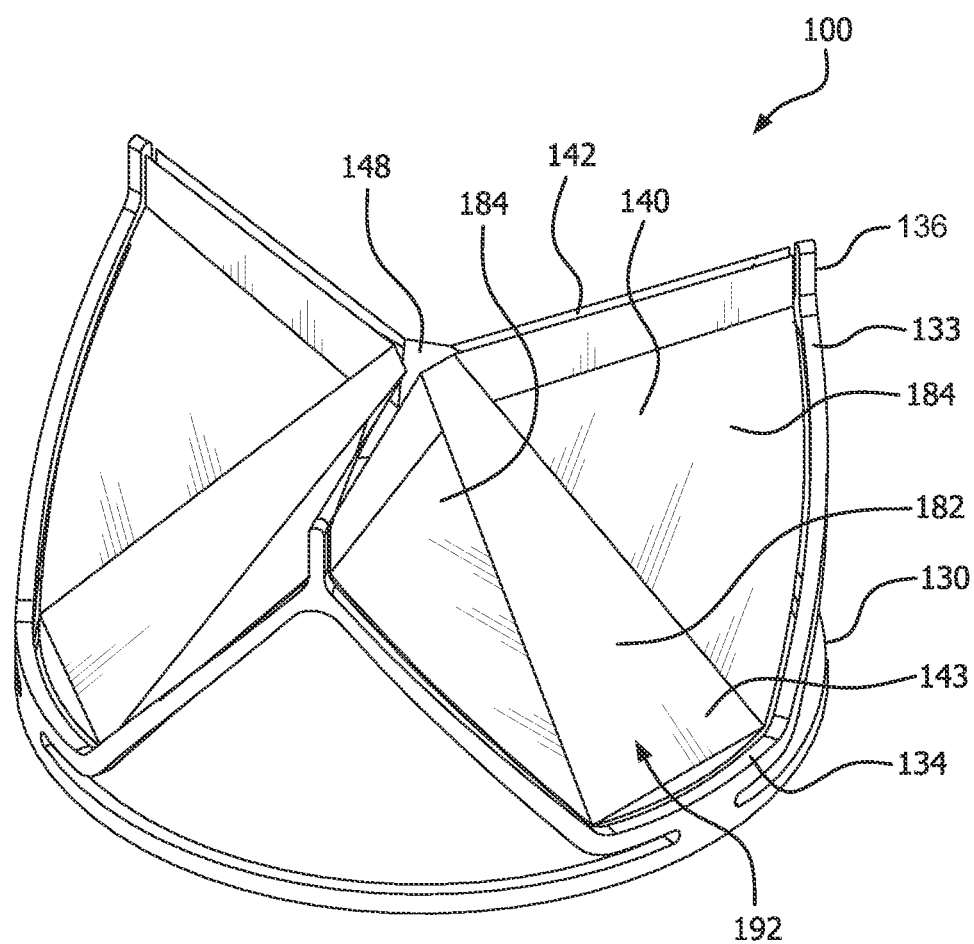
FIG. 1B is a perspective view of the embodiment of the valve of FIG. 1A.
Figure 1C:
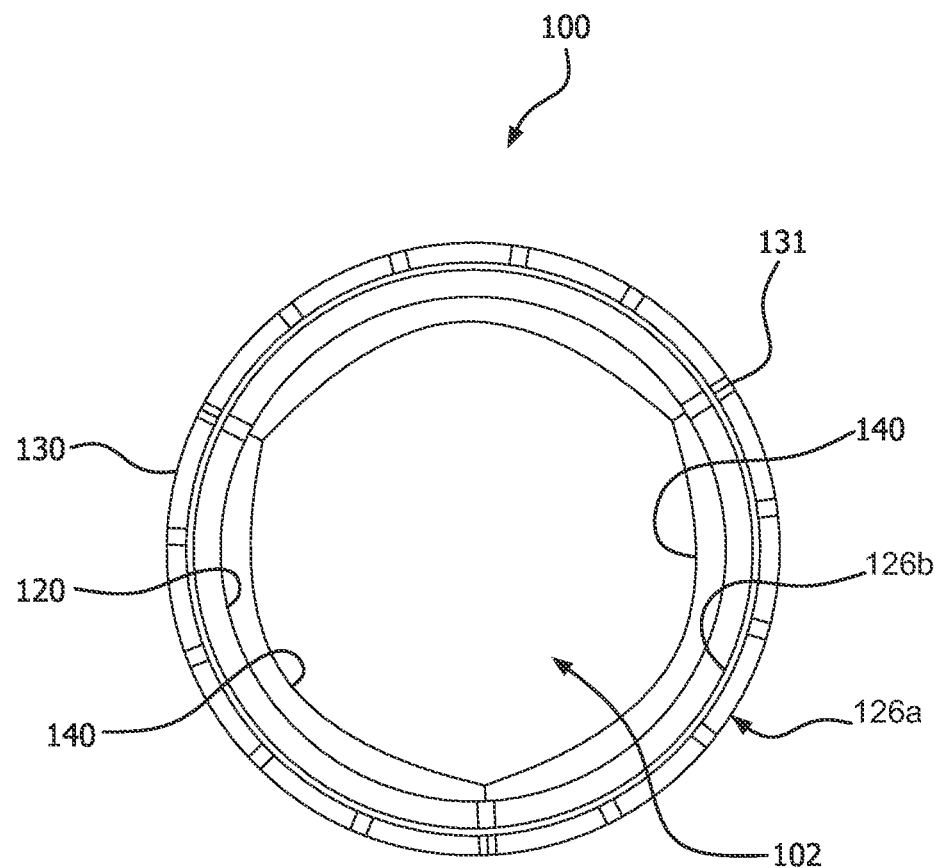
FIG. 1C is an axial view of an embodiment of the prosthetic valve of FIG. 2A in an open configuration.
Figure 1D:
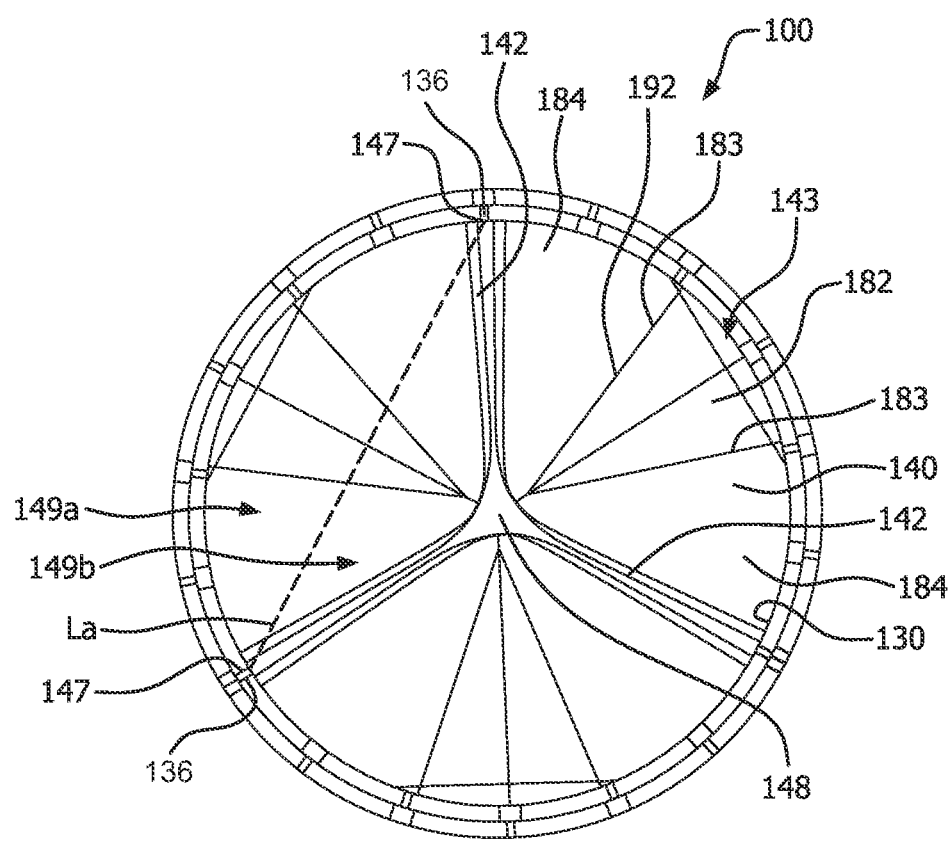
FIG. 1D is an axial view of the embodiment of the prosthetic valve of FIG. 2A in a closed configuration.
Figure 2:
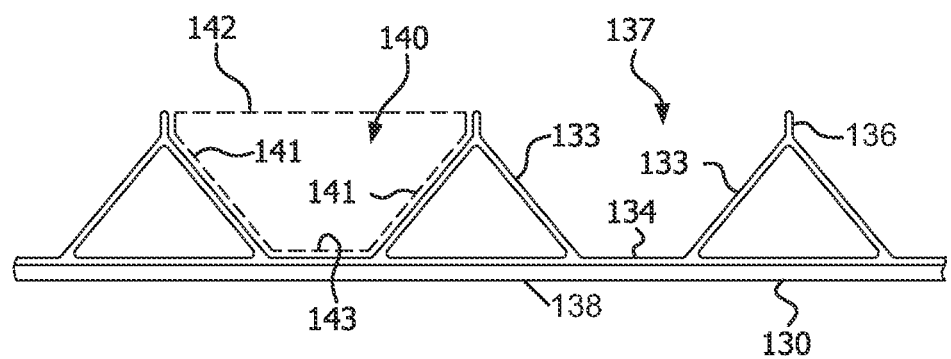
FIG. 2 is a representation of an embodiment of a leaflet frame unrolled to a flat orientation.

FIG. 1A is a side view of a valve 100, in accordance with an embodiment. FIG. 1B is a perspective view of the valve 100 of FIG. 1A. FIGS. 1C and 1D are axial views of the valve 100 of FIG. 1A in an open and closed configuration, respectively. The valve 100 comprises a leaflet frame 130 and film 160 that defines leaflets 140. FIG. 2 is a side view of the leaflet frame 130 of the valve 100 of FIG. 1A wherein the leaflet frame 130 has been longitudinally cut and laid open to better illustrate the elements of the generally tubular-shaped valve 100.

Leaflet Frame

Referring to FIGS. 1A-1D, the leaflet frame 130 is a generally tubular member defining a generally open pattern of apertures 122, in accordance with an embodiment. In accordance with transcatheter embodiments, the leaflet frame 130 is operable to allow it to be compressed and expanded between different diameters. The leaflet frame 130 comprises a frame first end 121a and a frame second end 121b opposite the frame first end 121a. The leaflet frame 130 comprises a leaflet frame outer surface 126a and a leaflet frame inner surface 126b opposite the leaflet frame outer surface 126a, as shown in FIG. 1A. The leaflet frame 130 defines commissure posts 136 that couple to the leaflet free edges 142.

Figure 4:
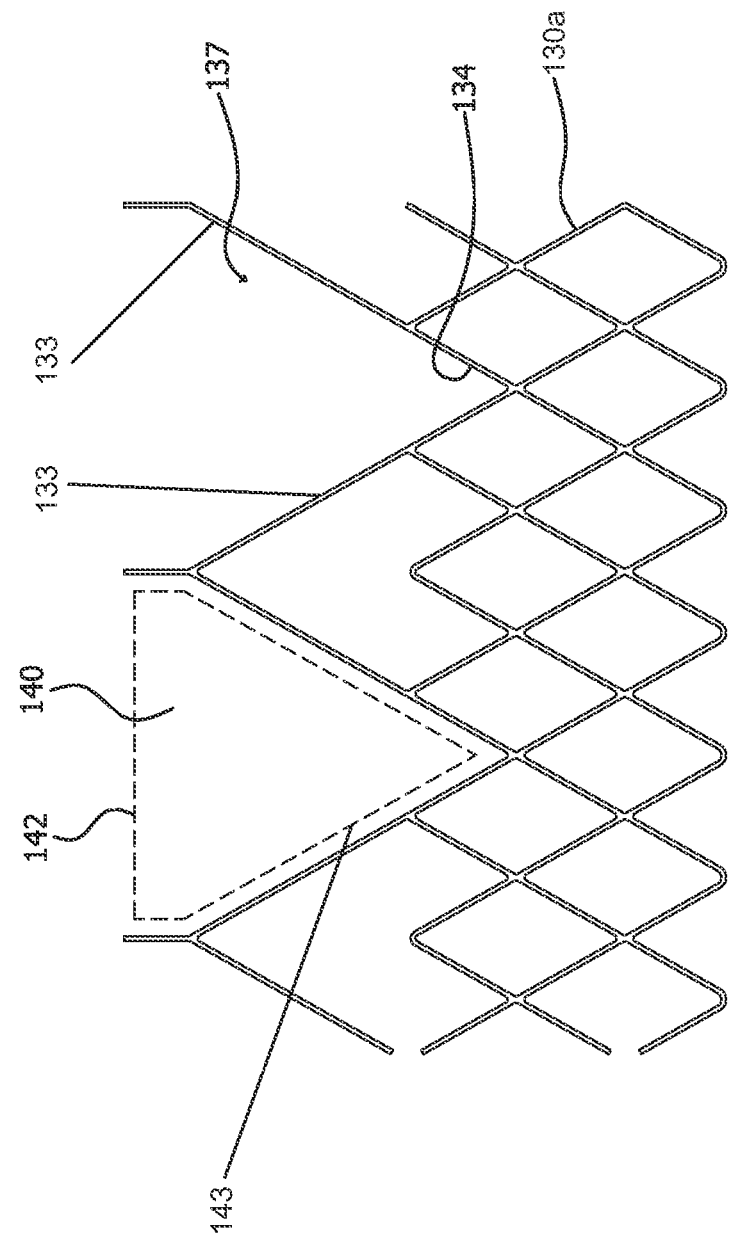
FIG. 4 is a representation of an embodiment of a leaflet frame unrolled to a flat orientation.

FIG. 4 is a side view of a leaflet frame 130a of a valve 100 wherein the leaflet frame 130a has been longitudinally cut and laid open to better illustrate the elements of the generally tubular-shaped frame 130a, in accordance with an embodiment. The leaflet frame 130a comprises angular frame elements suitable for affecting compression and expansion as would be needed for intravascular placement.

The leaflet frame 130 can define any number of features, repeatable or otherwise, such as geometric shapes and/or linear or meandering series of sinusoids. Geometric shapes can comprise any shape that facilitates substantially uniform circumferential compression and expansion. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

It is known that stents of various designs may be elastically deformable so as to be self-expanding under spring loads. It is also known that stents of various designs may be plastically deformable so as to be mechanically expanded such as with a balloon. It is also known that stents of various designs may be plastically deformable as well as elastically deformable. The embodiments of the outer frame 120 presented herein are not to be limited to a specific stent design or mode of expansion.

The frame 120 can comprise any metallic or polymeric biocompatible material. For example, the frame 120 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 3A:
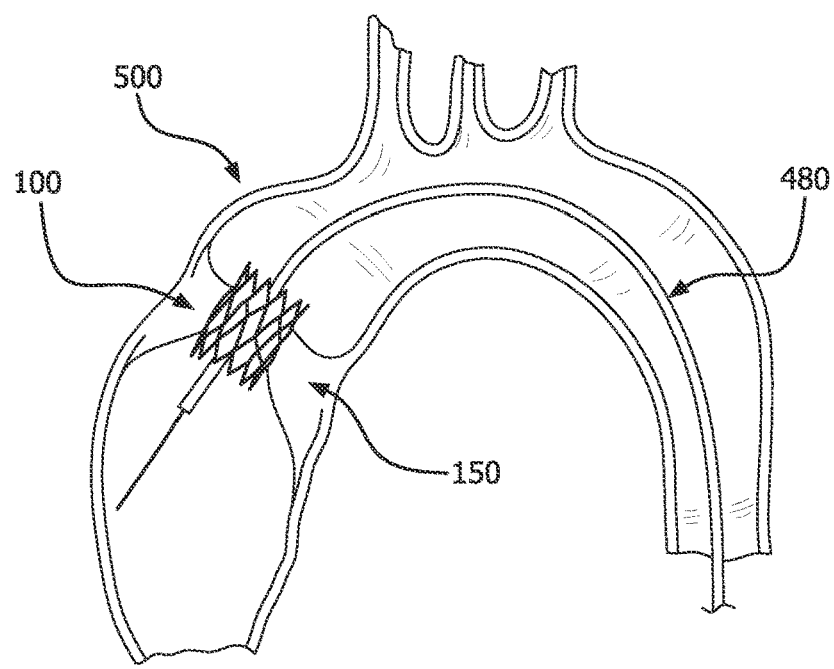
FIG. 3A is a side view of an embodiment of a transcatheter delivery system within anatomy.

In accordance with embodiments, the leaflet frame 130 can be configured to provide positive engagement with an implant site to firmly anchor the valve 100 to the site, as shown in FIG. 3A representing a transcatheter deployment of the valve 100. In accordance with an embodiment, the leaflet frame 130 can comprise a sufficiently rigid frame having small elastic recoil so as to maintain sufficient apposition against a tissue orifice 150 to maintain position. In accordance with another embodiment, the leaflet frame 130 can be configured to expand to a diameter that is larger than a tissue orifice 150 so that when valve 100 expands into the tissue orifice 150, it can be firmly seated therein. In accordance with another embodiment, the leaflet frame 130 can comprise one or more anchors (not shown) configured to engage the implant site, such as a tissue orifice 150, to secure the valve 100 to the implant site.

It is appreciated that other elements or means for coupling the valve 100 to an implant site are anticipated. By way of example, but not limited thereto, other means, such as mechanical and adhesive means may be used to couple the valve 100 to a synthetic or biological conduit.

As will be discussed later, the surgical valve 100 embodiment may or may not have the zigzag configuration since the surgical valve 100 may be of a fixed diameter and need not be operable to compress and re-expand.

Film

The film 160 is generally any sheet-like material that is biologically compatible and configured to couple to leaflets to the frame, in accordance with embodiments. It is understood that the term "film" is used generically for one or more biocompatible materials suitable for a particular purpose. The leaflets 140 are also comprised of the film 160.

In accordance with an embodiment, the biocompatible material is a film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

Details of various types of film 160 are discussed below. In an embodiment, the film 160 may be formed from a generally tubular material to at least partially cover the outer frame 120 and the inner frame 130. The film 160 can comprise one or more of a membrane, composite material, or laminate. Details of various types of film 160 are discussed below.

In an embodiment, the film 160 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 μm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Leaflet

In embodiments provided herein, a coaptation feature 196 is provided that allows a broad coaptation zone 198 defined by the leaflets adjacent to the leaflet free edges 142 when the leaflets are in a closed position. Referring to FIG. 1A of the closed valve 100, the leaflet is defined by a leaflet base 143, a free edge 142 and two leaflet sides 145 extending from the leaflet base 145 to the free edge 142. The coaptation zone 198 is that area of a leaflet 140 that is in contact with an adjacent leaflet 140. A coaptation height Hc is defined as that length measured in the axial direction along axis X of the leaflet that is in contact with an adjacent leaflet 140. Generally, the coaptation height Hc is measured from the leaflet free edge 142 to a location away from the leaflet free edge 142 where the adjacent leaflets 140 are no longer in contact. It is understood that the coaptation height Hc may vary across the leaflet free edge 142.

A broad coaptation zone 198 is desirable for, among other things to ensure full coaptation of the leaflets 140 in the case of a transcatheter valve 100 being placed in an out-of-round native orifice location that may result in an out-of-round valve frame 130 once expanded. In the out-of-round state, the leaflet free edges 142 may not properly come into contact with adjacent leaflet free edges 142. If complete coaptation is not achieved, regurgitant flow will result through the leaflet free edges 142 at the uncoapted locations.

A broad coaptation zone is also desirable for, among other things to prevent prolapse of the leaflets 140.

Though other leaflet geometry factors also contribute, prolapse can occur when no coaptation height Hc is present, wherein the contact between adjacent leaflets when the valve 100 is closed. In this case very little load sharing between the leaflets 140 occurs during full back pressure and the leaflets 140 can prolapse and not seal.

Figure 5:
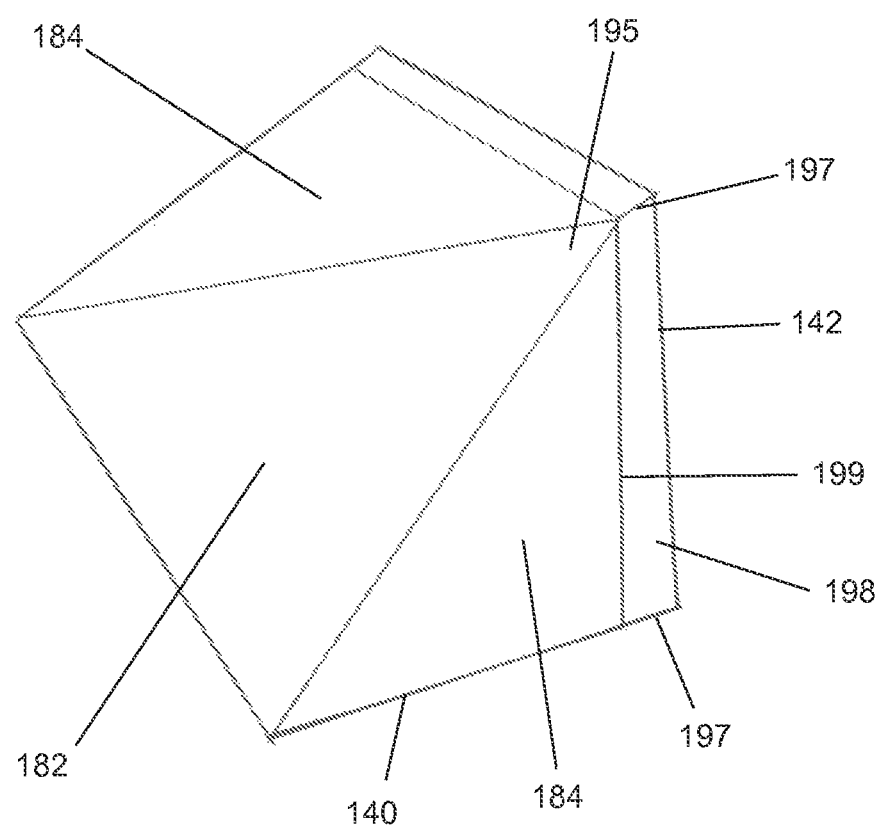
FIG. 5 is a perspective view of a leaflet in accordance with another embodiment.

FIG. 5 is a perspective view of a leaflet 140 comprising a vertical portion 197 that has been molded adjacent to the leaflet free edge 142 defined by a fold line 199 and the leaflet free edge 142. In contrast to embodiments presented herein, the central region 182 does not comprise a truncated top; that is, the triangular planar portion defines an apex 195 with zero width, with the vertical portion 197 extending therefrom. In thin, high-modulus materials however, this configuration results in a permanent fold that causes a resistance to bending with resultant poor hemodynamics.

Referring to FIGS. 1A, 1B, and 2, each leaflet window 137 is provided with a biocompatible material, such as a film 160, which is coupled to a portion of the leaflet window sides 133 with the film 160 defining a leaflet 140. Each leaflet 140 defines a leaflet free edge 142 and a leaflet base 143, in accordance with an embodiment. As will be described below, it is anticipated that a plurality of embodiments of leaflet base configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134. In accordance with another embodiment, the film 160 is coupled to a portion of the leaflet window sides When the leaflets 140 are in a fully open position, the valve 100 presents a substantially circular valve orifice 102 as shown in FIG. 1C. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the valve 100 is closed, generally about half of each leaflet free edge 142 abuts an adjacent half of a leaflet free edge 142 of an adjacent leaflet 140, as shown in FIG. 1D. The three leaflets 140 of the embodiment of FIG. 1D meet at a triple point 148. The valve orifice 102 is occluded when the leaflets 140 are in the closed position stopping fluid flow.

Referring to FIG. 1D, in accordance with an embodiment, each leaflet 140 includes a central region 182 and two side regions 184 on opposite sides of the central region 182. The central region 182 is defined by a shape substantially that of a triangle defined by two central region sides 183, the leaflet base 143 and the free edge 142. The two central region sides 183 converge from the leaflet base 143 to the free edge 142.

In accordance with an embodiment, the central region 182 is substantially planar, defining a planar zone 192, when the valve 100 is in the closed position and not under fluid pressure. The planar zone 192 has a shape substantially of an isosceles triangle with apices extending to the leaflet frame 130. Referring to FIG. 1D, an apex line La is indicated connecting the apices 147 of the leaflets 140. The apex line La divides the leaflet 140 into a first region 149*a* adjacent the leaflet frame 130, and a second region 149*b* adjacent the leaflet free edge. The first region 149*a* contains a larger proportion of planar zone 192 than the second region 149*b*. In other embodiments, the majority of the planar zone 192 of each leaflet 140 is located inferior and exterior to apex line La joining the apices of two adjacent commissure posts 136. The ratio of area of the planar zone 192 distributed in the first region 149*a* and second region 149*b* has been found to produce better leaflet opening dynamics than if there were more area of the planar zone 192 distributed in the second region 149*b* than the first region 149*a*.

As shown in FIG. 1A, in accordance with an embodiment, the planar zone 192 has a shape substantially of an isosceles triangle with apices extending to the leaflet frame 130. The planar zone 192 extends to the free edge 142 of the leaflet 140 defining a truncated top 193 of the isosceles triangle having a width Hp. As shown, therefore, the planar zone 192 has a truncated top 193 with a width Hp greater than zero.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

In accordance with an embodiment of a valve 100 suitable for transcatheter placement, the valve 100 may be compressed into a collapsed configuration having a smaller diameter and expanded into an expanded configuration so that the valve 100 can be delivered via catheter in the collapsed configuration and expanded upon deployment within the tissue orifice 150 as shown in FIG. 3A. The leaflet frame 130 can be operable to recover circumferential uniformity when transitioning from the collapsed configuration to the expanded configuration.

The valve 100 may be mounted onto a delivery catheter, suitable for a particular purpose. The diameter of the valve 100 in the collapsed configuration is determined in part by the thickness of the frame and the leaflet thickness.

Other Considerations

In accordance with an embodiment, the valve 100 can be configured to prevent interference with a heart conduction system by not covering a bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the expanded, functional diameter. However, the valve 100 can be constructed at any length and, more generally, any desirable dimension.

In a transcatheter embodiment, in a collapsed state, the valve 100 can have a collapsed profile that is less than about 35% of the expanded profile. For example, the valve 100 comprising a 26 mm expanded diameter can have a collapsed diameter of less than about 8 mm, or less than about 6 mm. The percent difference in diameter is dependent on dimensions and materials of the valve 100 and its various applications, and therefore, the actual percent difference is not limited by this disclosure.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 3A, a valve delivery system 500 comprises a valve 100 having a collapsed configuration and an expanded configuration as previously described and an elongated flexible catheter 480, such as a balloon catheter, configured to deploy the valve 100 via catheter. The catheter 480 can comprise a balloon to expand the valve 100 and/or if required, to touch up the valve 100 to ensure proper seating. The valve 100 can be mounted to the distal section of the catheter 480 for delivery through the vasculature. In order to hold the valve in a collapsed configuration on the catheter 480, the valve delivery system may further comprise a removable sheath (not shown) to closely fit over the transcatheter valve 100.

A method of delivery can comprise the steps of radially compressing a valve into its collapsed configuration onto the distal end of an elongate flexible catheter having proximal and distal ends; delivering the valve to a tissue orifice, such as a native aortic valve orifice, via a transfemoral or transapical route, and expanding the valve into the tissue orifice. The valve can be expanded by inflating a balloon.

A method of delivery can comprise the steps of radially compressing a valve into its collapsed configuration, onto the distal section of an elongated flexible catheter having proximal and distal ends. A restraint, which can be connected to a tether that passes through the orifice of valve and the lumen of the catheter, is fitted around the posts of the valve. The valve is then delivered to a native valve orifice, such as a native aortic valve orifice, via a route of delivery and expanded into the native orifice. The route of delivery can comprise a transfemoral or transapical route. The valve can be expanded by inflating a balloon.

Surgical Embodiments

Figure 3B:
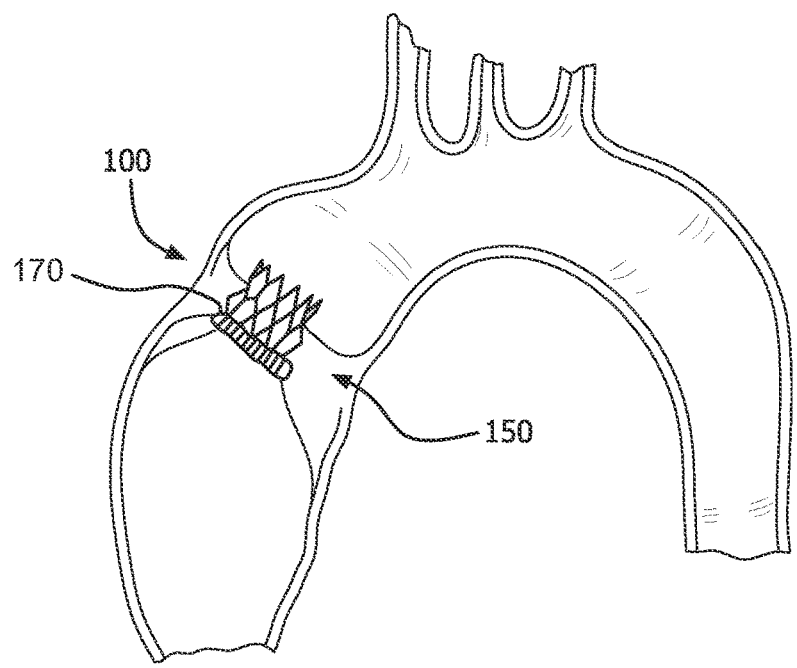
FIG. 3B is a side view of an embodiment of a surgical valve within anatomy.

It is appreciated that the embodiments of the valve 100 may be surgically implanted rather than using transcatheter techniques. Embodiments of a surgically implanted valve 100 may be substantially the same as those described above, with the addition of a sewing cuff 170 adjacent to the leaflet frame outer surface 126a, shown in FIG. 3B, in accordance with an embodiment. The sewing cuff, which is well known in the art, is operable to provide structure that receives suture for coupling the valve 100 to an implant site, such as the tissue orifice. The sewing cuff may comprise any suitable material, such as, but not limited to, double velour polyester.

The sewing cuff may be located circumferentially around the leaflet frame 130 or perivalvular depending from the leaflet frame 130.

Method of Making

Figure 6:
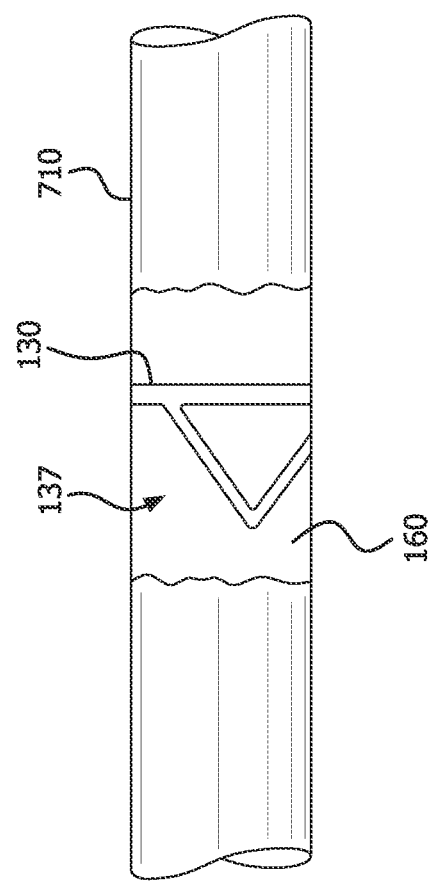
FIG. 6 is a side view of the leaflet frame on an assembly mandrel, in accordance with an embodiment.

Embodiments described herein also pertain to a method of making the valve 100 embodiments as described herein. In order to make the various embodiments, a cylindrical mandrel 710 can be used. With reference to FIG. 6, the mandrel 710 comprises a structural form operable to receive the leaflet frame 130 thereon.

Embodiments described herein also pertain to a method of making the valve 100 embodiments as described herein. In order to make the various embodiments, a cylindrical mandrel 710 can be used. With reference to FIG. 6, the mandrel 710 comprises a structural form operable to receive the leaflet frame 130 thereon. An embodiment of a method of making a valve 100 comprises the steps of wrapping a first layer of film 160, e.g., a composite as described herein, into a tubular form about the mandrel 710; placing the leaflet frame 130 over the first layer of film 160, as shown in FIG. 6; forming a second layer of film 160 over the leaflet frame 130; thermally setting the assembly; receiving the assembly over a cutting mandrel 712 as shown in FIGS. 8A and 8B; cutting the film 160 across the leaflet window top within the leaflet window 137

Example

In exemplary embodiments, a heart valve having polymeric leaflets formed from a composite material having an expanded fluoropolymer membrane and an elastomeric material and joined to a semi-rigid, non-collapsible metallic frame, and further a having strain relief was constructed according to the following process:

A leaflet frame 130 was laser machined from a length of MP35N cobalt chromium tube hard tempered with an outside diameter of 26.0 mm and a wall thickness of 0.6 mm in the shape. The leaflet frame was electro-polished resulting in 0.0127 mm material removal from each surface and leaving the edges rounded. The leaflet frame was exposed to a surface roughening step to improve adherence of leaflets to the leaflet frame. The leaflet frame was cleaned by submersion in an ultrasonic bath of acetone for approximately five minutes. The entire metal frame surface was then subjected to a plasma treatment using equipment (e.g. PVA TePLa America, Inc Plasma Pen, Corona, Calif.) and methods commonly known to those having ordinary skill in the art. This treatment also served to improve the wetting of the fluorinated ethylene propylene (FEP) adhesive.

FEP powder (Daikin America, Orangeburg N.Y.) was then applied to the leaflet frame. More specifically, the FEP powder was stirred to form an airborne "cloud" in an enclosed blending apparatus, such as a standard kitchen type blender, while the leaflet frame is suspended in the cloud. The leaflet frame was exposed to the FEP powder cloud until a layer of powder was adhered to the entire surface of the leaflet frame. The leaflet frame was then subjected to a thermal treatment by placing it in a forced air oven set to 320° C. for approximately three minutes. This caused the powder to melt and adhere as a thin coating over the entire leaflet frame. The leaflet frame was removed from the oven and left to cool to approximately room temperature.

The strain relief was attached to the leaflet frame in the following manner. A thin (122 μm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C. and heated for 20 min. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990μ) walled partially sintered 22 mm inner diameter ePTFE tube (density=0.3 g/cm$^3$) was disposed onto the 24.5 mm vented metal mandrel with release liner. The ePTFE tube inner diameter was enlarged by stretching it on a tapered mandrel to accommodate the larger mandrel diameter.

A thin (4 μm) film of type 1 FEP (ASTM D3368) was constructed using melt extrusion and stretching. One layer of the FEP was wrapped over the 5 cm length of the ePTFE tube.

The FEP powder coated leaflet frame was disposed onto the vented metal mandrel generally in the middle of the 5 cm span of ePTFE tube and FEP film.

One layer of the FEP was wrapped over the leaflet frame and 5 cm length of the ePTFE tube.

A second 5 cm length of the 990 μm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore Rastex® Sewing Thread, Part #S024T2, Newark Del.) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 min such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

A leaflet material was then prepared. A membrane of ePTFE was manufactured according to the general teachings described in U.S. Pat. No. 7,306,729. The ePTFE membrane had a mass per area of 0.452 g/m$^2$, a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, Minn.) in a 2.5% concentration. The solution was coated using a mayer bar onto the ePTFE membrane (while being supported by a polypropylene release film) and dried in a convection oven set to 145° C. for 30 seconds.

After 2 coating steps, the final ePTFE/fluoroelastomer or composite had a mass per area of 1.75 g/m², 29.3% fluoropolymer by weight, a dome burst strength of about 8.6 KPa, and thickness of 0.81 µm.

The leaflet material was then attached in a cylindrical or tubular shape to the valve frame encapsulated with polymeric material defining a strain relief in the following manner. A release liner was disposed on a 24.5 mm vented mandrel and perforated using a scalpel blade to communicate pressure between the vent holes in the mandrel.

The leaflet frame with polymeric strain relief was disposed onto the release liner covering the vented metal mandrel generally in the middle of the 100 cm span of the mandrel.

Sixty-two layers of leaflet material were wrapped over the leaflet frame and 100 cm length of the mandrel. Excess leaflet material was trimmed away with a scalpel from the mandrel adjacent to the vent holes.

A sacrificial tube was placed over the assembly and Rastex® fiber was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 23 minutes such that the mandrel temperature reached approximately 285° C. (as measured by a thermocouple direct contact with the inner diameter of the mandrel). The assembly was removed from the oven and allowed to cool to approximately room temperature while still under 100 psi pressure and vacuum.

The Rastex® fiber and sacrificial tube were then removed. Approximately 30 psi of pressure was applied to the inside of the mandrel to assist in removal of the assembly. The inner release liner was peeled away from the internal diameter of the assembly by inverting the liner and axially pulling it apart.

The cylindrical shape of the leaflet frame and leaflet assembly was then molded into the final closed leaflet geometry in the following manner. The assembly was placed onto a 24.5 mm vented mandrel with a cavity defining the closed geometry of the leaflets.

Rastex® fiber was used to seal both ends of the leaflet tube against the circumferential grooves in the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 23 minutes such that the mandrel temperature reached approximately 285° C. (as measured by a thermocouple direct contact with the inner diameter of the mandrel). The assembly was removed from the oven and allowed to cool to approximately room temperature while still under 100 psi pressure and vacuum. The Rastex® fiber was then removed and approximately 10 psi of pressure was applied to the internal diameter of the mandrel to assist in removal of the assembly.

Figure 7A:
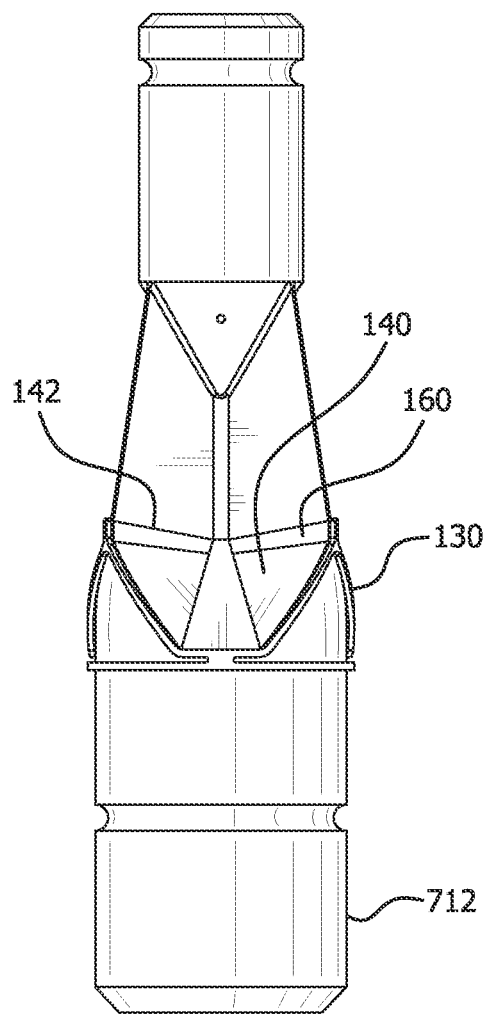
FIG. 7A is a side view of the leaflet frame on a cutting mandrel, in accordance with an embodiment.
Figure 7B:
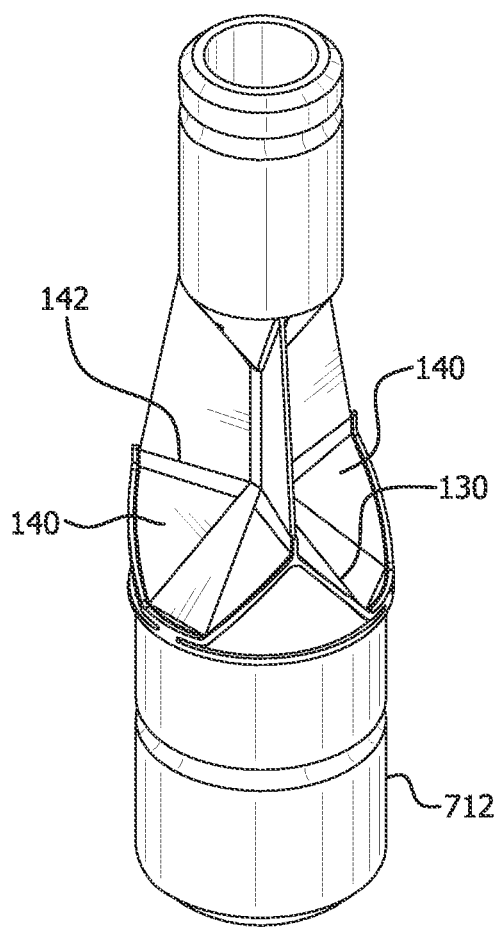
FIG. 7B is a perspective view of the leaflet frame on the assembly mandrel of FIG. 7A.

Excess leaflet material was trimmed generally along the free edge line depicted in a cavity mold 714 of the cutting mandrel 712 shown in FIGS. 7A and 7B. The final leaflet was comprised of 28.22% fluoropolymer by weight with a thickness of 50.3 µm. Each leaflet had 62 layers of the composite and a ratio of thickness/number of layers of 0.81 µm.

The resulting valve included leaflets formed from a composite material with more than one fluoropolymer layer having a plurality of pores and an elastomer present in substantially all of the pores of the more than one fluoropolymer layer. Each leaflet was movable between a closed position, shown illustratively in FIG. 1D, in which fluid was substantially prevented from flowing through the valve, and an open position, shown illustratively in FIG. 1C, in which fluid was allowed to flow through the valve.

The performance of the valve leaflets was characterized on a real-time pulse duplicator that measured typical anatomical pressures and flows across the valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada)

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm² cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve under test.

The heart flow pulse duplicator system was adjusted to produce the desired flow (5 L/minutes), mean pressure (15 mmHg), and simulated pulse rate (70 bpm). The valve under test was then cycled for about 5 to 20 minutes.

Pressure and flow data were measured and collected during the test period, including right ventricular pressures, pulmonary pressures, flow rates, and pump piston position. Parameters used to characterize the valve are effective orifice area and regurgitant fraction. The effective orifice area (EOA), which can be calculated as follows: $EOA(cm^2) = Q_{rms}/(51.6*(\Delta P)^{1/2})$ where $Q_{rms}$ is the root mean square systolic/diastolic flow rate (cm³/s) and $\Delta P$ is the mean systolic/diastolic pressure drop (mmHg).

Another measure of the hydrodynamic performance of a valve is the regurgitant fraction, which is the amount of fluid or blood regurgitated through the valve divided by the stroke volume.

The hydrodynamic performance was measured prior to accelerated wear testing. The performance values were; EOA=2.4 cm² and regurgitant fraction=11.94%.

As used in this application, the surface area per unit mass, expressed in units of m²/g, was measured using the Brunauer-Emmett-Teller (BET) method on a Coulter SA3100Gas Adsorption Analyzer, Beckman Coulter Inc. Fullerton Calif., USA. To perform the measurement, a sample was cut from the center of the expanded fluoropolymer membrane and placed into a small sample tube. The mass of the sample was approximately 0.1 to 0.2 g. The tube was placed into the Coulter SA-Prep Surface Area Outgasser (Model SA-Prep, P/n 5102014) from Beckman Coulter, Fullerton Calif., USA and purged at about 110° C. for about two hours with helium. The sample tube was then removed from the SA-Prep Outgasser and weighed. The sample tube was then placed into the SA3100 Gas adsorption Analyzer and the BET surface area analysis was run in accordance with the instrument instructions using helium to calculate the free space and nitrogen as the adsorbate gas.

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

The presence of elastomer within the pores can be determined by several methods known to those having ordinary skill in the art, such as surface and/or cross section visual, or other analyses. These analyses can be performed prior to and after the removal of elastomer from the leaflet.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho=m/w*l*t$, in which: $\rho$=density (g/cm$^3$): m=mass (g), w=width (cm), l=length (cm), and t=thickness (cm. The average of three measurements was reported.

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For longitudinal measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness measured using the Käfer FZ1000/30 snap gauge. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), wherein the bulk density of the PTFE was taken to be about 2.2 g/cm$^3$. Flexural stiffness was measured by following the general procedures set forth in ASTM D790. Unless large test specimens are available, the test specimen must be scaled down. The test conditions were as follows. The leaflet specimens were measured on a three-point bending test apparatus employing sharp posts placed horizontally about 5.08 mm from one another. An about 1.34 mm diameter steel bar weighing about 80 mg was used to cause deflection in the y (downward) direction, and the specimens were not restrained in the x direction. The steel bar was slowly placed on the center point of the membrane specimen. After waiting about 5 minutes, the y deflection was measured. Deflection of elastic beams supported as above can be represented by: $d=F*L^3/48*EI$, where F (in Newtons) is the load applied at the center of the beam length, L (meters), so L=½ distance between suspending posts, and EI is the bending stiffness (Nm). From this relationship the value of EI can be calculated. For a rectangular cross-section: $I=t^3*w/12$, where I=cross-sectional moment of inertia, t=specimen thickness (meters), w=specimen width (meters). With this relationship, the average modulus of elasticity over the measured range of bending deflection can be calculated.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed is:
1. A prosthetic valve comprising:
a leaflet frame; and
a plurality of leaflets coupled to the leaflet frame, each leaflet having a center, each leaflet including a leaflet free edge and a leaflet base opposite from the leaflet free edge, wherein each of the plurality of leaflets flexes about the respective leaflet base of the plurality of leaflets and each leaflet having a planar zone including the center of the leaflet and being without creases or folds, wherein the planar zone is planar, wherein the planar zone defines a shape having an area, wherein the area is larger nearer the leaflet base than the leaflet free edge, wherein the planar zone extends to the leaflet free edge defining a truncated top having a top width as measured along the leaflet free edge greater than zero, each leaflet having a coaptation zone defined by an area adjacent the leaflet free edge that is in contact with an adjacent leaflet when the leaflets are in a closed position and a vertical coaptation zone defining a coaptation height as a length of the coaptation zone measured in an axial direction, wherein the coaptation height is greater than a thickness of the leaflet, wherein the planar zone not including the vertical coaptation zone is planar when the prosthetic valve is in a closed position under unpressurized conditions.

2. The prosthetic valve of claim 1, the leaflet frame having a tubular shape, the leaflet frame defining a plurality of leaflet windows wherein each of the leaflet windows includes two leaflet window sides, and a leaflet window base, two adjacent leaflet window sides terminating at a commissure post, a majority of the planar zone of each leaflet being located exterior to a line joining apices of two adjacent commissure posts.

3. The prosthetic valve of claim 2, wherein the leaflet frame comprises a leaflet frame first end and a leaflet frame second end opposite the leaflet frame first end, each leaflet window having a shape determined, at least in part, by wrapping a two dimensional isosceles trapezoid onto a tubular shape of the leaflet frame, the isosceles trapezoid having a base and two sides that diverge from the base, and wherein a side from adjacent isosceles trapezoids meet at the leaflet frame second end.

4. The prosthetic valve of claim 3, further comprising a vertical element extending from where the adjacent isosceles trapezoids meet, the vertical element having a length extending to the leaflet frame second end.

5. The prosthetic valve of claim 1, wherein each planar zone has a shape of an isosceles trapezoid.

6. The prosthetic valve of claim 1, wherein each leaflet has a shape of an isosceles trapezoid having two leaflet sides, a leaflet base and a leaflet free edge.

7. The prosthetic valve of claim 1, wherein the leaflet frame has a tubular shape, the leaflet frame defining a plurality of leaflet windows wherein each of the leaflet windows includes two leaflet window sides and a leaflet window base, wherein for each leaflet and its respective leaflet window the leaflet base is coupled to the leaflet window base and two leaflet sides are coupled to one of the two leaflet window sides, and the planar zone extends to the leaflet base.

8. The prosthetic valve of claim 1, the leaflet frame having a tubular shape, the leaflet frame defining a plurality of leaflet windows wherein each of the leaflet windows includes two leaflet window sides, a leaflet window base, and a leaflet window top; and
   a film coupled to the leaflet frame and defining at least one of the leaflets extending from each of the leaflet windows, wherein each leaflet has a shape of an isosceles trapezoid having two leaflet window sides, the leaflet base and the leaflet free edge, wherein the two leaflet sides diverge from the leaflet base, wherein each leaflet base is flat, wherein for each leaflet and its respective leaflet window the leaflet ease is coupled to the leaflet window base and wherein each of the two leaflet sides are coupled to one of the two window sides.

9. The prosthetic valve of claim 8, wherein the film is coupled to an outer surface of the leaflet frame, wherein the film defines each leaflet extending from its respective leaflet window.

10. The prosthetic valve of claim 8, wherein the film is coupled to an inner surface of the leaflet frame, wherein the film defines each leaflet extending from its respective leaflet window.

11. The prosthetic valve of claim 8, wherein the film is coupled to an inner surface and an outer surface of the leaflet frame, wherein the film defines each leaflet extending from its respective leaflet window.

12. The prosthetic valve of claim 1, wherein each leaflet is defined by two leaflet sides, the leaflet base and the leaflet free edge, wherein each leaflet includes a central region and two side regions on opposite sides of the central region, wherein each central region is defined by a shape of an isosceles trapezoid defined by two central region sides, the leaflet base and the leaflet free edge, wherein the two central region sides converge from the leaflet base, and wherein each of the side regions have a shape of a triangle and are defined by one of the central region sides, one of the leaflet sides, and the leaflet free edge, wherein the central region is planar.

13. The prosthetic valve of claim 12, wherein for each leaflet each of the two side regions and the central region are planar when the prosthetic valve is in the closed position under unpressurized conditions.

14. The prosthetic valve of claim 1, wherein a leaflet window side of one leaflet window is interconnected with a leaflet window side of an adjacent leaflet window.

15. The prosthetic valve of claim 1, wherein the leaflet frame comprises a plurality of spaced apart interconnected leaflet windows, each leaflet window defining an isosceles trapezoid, wherein each leaflet window side is defined by two sides of the isosceles trapezoid, and wherein each leaflet window comprises a base defined by a base element.

16. The prosthetic valve of claim 1, wherein the prosthetic valve comprises a collapsed configuration and an expanded configuration for transcatheter delivery.

17. The prosthetic valve of claim 1, wherein each leaflet comprises a polymeric material.

18. The prosthetic valve of claim 17, wherein each leaflet comprises a laminate.

19. The prosthetic valve of claim 18, wherein the laminate has more than one layer of a fluoropolymer membrane.

20. The prosthetic valve of claim 1, wherein each leaflet comprises a film having at least one fluoropolymer membrane layer having a plurality of pores and an elastomer present in the pores of at least one layer of fluoropolymer membrane.

21. The prosthetic valve of claim 20, wherein the film comprises less than about 80% fluoropolymer membrane by weight.

22. The prosthetic valve of claim 20, wherein the elastomer comprises (per)fluoroalkylvinylethers (PAVE).

23. The prosthetic valve of claim 20, wherein the elastomer comprises a copolymer of tetrafluoroethylene and perfluoromethyl vinyl ether.

24. The prosthetic valve of claim 20, wherein the fluoropolymer membrane comprises ePTFE.

* * * * *